United States Patent [19]

Wilson

[11] 4,331,518

[45] May 25, 1982

[54] BISMUTH COMPOSITION, METHOD OF ELECTROPLATING A TIN-BISMUTH ALLOY AND ELECTROPLATING BATH THEREFOR

[75] Inventor: Harold P. Wilson, Huron, Ohio

[73] Assignee: Vulcan Materials Company, Birmingham, Ala.

[21] Appl. No.: 223,713

[22] Filed: Jan. 9, 1981

[51] Int. Cl.$^3$ ............................ C25D 3/60; C07F 9/94
[52] U.S. Cl. .................................... 204/43 S; 260/447
[58] Field of Search ............................ 204/43 S, 45 R; 260/447

[56] References Cited

U.S. PATENT DOCUMENTS

| Re. 29,239 | 5/1977 | Hyner et al. | 75/175 R |
|---|---|---|---|
| 1,964,696 | 6/1934 | Traube et al. | 260/447 X |
| 2,683,114 | 7/1954 | Little | 204/45 A |
| 2,721,836 | 10/1955 | Du Rose | 204/45 A |
| 2,801,959 | 8/1957 | Du Rose | 204/45 A |
| 2,817,628 | 12/1957 | Breining et al. | 204/45 A |
| 3,616,291 | 10/1971 | Wilson | 204/27 |
| 3,616,292 | 10/1971 | Wilson | 204/28 |
| 3,663,384 | 5/1972 | Lescure | 204/43 S |
| 3,764,489 | 10/1973 | Zuntini et al. | 204/43 G |
| 4,162,205 | 7/1979 | Wilson et al. | 204/43 S |
| 4,163,700 | 8/1979 | Igarashi et al. | 204/43 S |
| 4,252,618 | 2/1981 | Grenda | 204/43 S |

FOREIGN PATENT DOCUMENTS 2050145  6/1971  Fed. Rep. of Germany .... 204/43 S

Primary Examiner—G. L. Kaplan
Attorney, Agent, or Firm—Burns, Doane, Swecker & Mathis

[57] ABSTRACT

An improved electrotinplating process and acidic electroplating bath therefor is disclosed. The acidic electroplating bath contains tin ions and a chelate salt comprising an acid bismuth sulfate gluconate. An improved electrotinplating process is therefore provided which produces an electroplated tin-bismuth alloy which is resistant to the effects of tin pest and the formation of tin whiskers.

23 Claims, No Drawings

BISMUTH COMPOSITION, METHOD OF ELECTROPLATING A TIN-BISMUTH ALLOY AND ELECTROPLATING BATH THEREFOR

BACKGROUND OF THE INVENTION

This invention relates to an improvement in the method of producing electrodeposits of tin, and is particularly concerned with the electrodeposition of tin deposits from a plating bath which are substantially immune to the effects of "tin pest" and the formation of "tin whiskers".

It has been found that when materials bearing an electrodeposit of tin are maintained under conditions wherein the ambient temperature is less than 18° C., the transformation of white (beta) tin of tetragonal form to the gray (alpha) tin of cubic centered form can occur. This transformation is commonly known as "tin disease" or "tin pest". The result of the transformation is such that the specific gravity of the tin or tin electroplate is lowered from about 7.3 to about 5.75 with its attendant destruction of the tin's metallic properties. As the tin pest develops, a loose tin powder is formed which easily separates from the base metal. The tin then loses its ability to protect the base metal. Accordingly, the base metal is more susceptible to the effects of corrosion.

In addition, the formation of "tin whiskers" in electrotinplate has been observed. Such a phenomenom appears to be more prevalent in electrotinplate produced from an acidic plating bath as opposed to electrotinplate produced from an alkaline stannate bath. The formation of such whiskers is highly undesirable, especially in tin plate intended for use in the electronics industry.

It is known that the presence of a small amount of bismuth in tin or tin electroplate inhibits the formation of tin pest. It has been reported that a concentration of bismuth above 0.12 percent in tin or tin alloy inhibits and may even prevent the formation of tin pest at temperatures as low as −73° C. for indefinite periods of time. See, for example, MacIntosh, R. M. "The Properties of Tin at Low Temperatures," Tin Research Institute, Columbus, Ohio (Oct. 15, 1953). The presence of bismuth in tin electroplate similarly reduces the occurrence of tin whisker formation. See Sabbagh, N. A. S. et al., "Tin Whiskers: Causes and Remedies", *Metal Finishing*, March, 1975.

It is also known that an alkali metal bismuth salt of a linear polyhydroxymonocarboxylic acid (such as a potassium bismuth gluconate) can be employed in an alkaline tin electroplating bath as a source of bismuth such that a tin-bismuth alloy may be produced. See U.S. Pat. No. 4,162,205, issued to Wilson et al on July 24, 1979. A need presently exists, however, to provide a means by which bismuth can be incorporated into tin electroplate during the formation thereof from an acidic tin electroplating bath.

OBJECTS AND SUMMARY OF THE INVENTION

It is an object of the present invention to provide an improved method for the electrodeposition of a tin-containing alloy.

It is also an object of the present invention to provide an improved method for the electrodeposition of a tin-bismuth alloy from an acidic plating bath.

It is still further an object of the present invention to provide an acidic electroplating solution which may be employed in the electrodeposition of a tin-bismuth alloy.

It is also an object of the present invention to obviate the disadvantages of the prior art as set forth above.

In accordance with one aspect of the present invention, there is provided a method for electroplating a tin-containing alloy onto a conductive substrate comprising immersing a conductive substrate to be plated into an aqueous acidic plating bath containing tin ions, free sulfuric acid, and a chelate salt comprising bismuth sulfate gluconate, and electroplating a tin and bismuth-containing alloy onto the conductive substrate as a cathode in the bath.

In accordance with another aspect of the present invention, there is provided a method of electroplating a tin and bismuth-containing alloy onto a conductive substrate comprising immersing a conductive substrate to be plated into an acidic aqueous plating bath containing tin ions in an amount ranging between about 10 to about 75 grams per liter, free sulfuric acid in an amount ranging between about 140 to about 215 grams per liter, and a chelate salt comprising bismuth sulfate gluconate in an amount ranging between about 0.06 to about 21.15 grams per liter expressed as bismuth metal, and electroplating a tin and bismuth-containing alloy onto said conductive substrate as a cathode in said bath.

In accordance with yet another aspect of the present invention, there is provided an aqueous acidic solution for plating a tin and bismuth-containing alloy onto a conductive substrate which solution comprises tin ions, free sulfuric acid and an acid chelate comprising bismuth sulfate gluconate.

In accordance with still yet another aspect of the present invention, there is provided a composition for use in the plating of a bismuth-containing alloy comprising an aqueous solution of a chelate salt comprising bismuth sulfate gluconate.

DETAILED DESCRIPTION OF THE INVENTION

It has now been found that a chelate salt comprising a bismuth sulfate gluconate may be employed in electroplating baths such as acidic tin electroplating baths to enable a bismuth-containing alloy (e.g., a tin-bismuth alloy) to be plated therefrom. The chelating gluconate supplies enough chelating power to increase the solubility of the bismuth in the solution to ensure that sufficient bismuth is incorporated in the tin electroplate such that the tin electroplate is rendered resistant to the effects of "tin pest" and the formation of "tin whiskers".

The bismuth-containing chelate salt of the present invention may be formed by dissolving bismuth trioxide in an agitated solution of gluconic acid at a temperature in the range of 30° to 100° C. or near the boiling point of the solution. Preferably, the temperature ranges from about 70° to about 80° C. Sulfuric acid is then added to the solution to form the bismuth sulfate gluconate.

The bismuth-containing chelate salt may also be formed by the addition of gluconic acid to a solution of bismuth sulfate $Bi_2(SO_4)_3$. For example, bismuth trioxide may be first dissolved in an agitated aqueous solution of sulfuric acid. Gluconic acid may then be added slowly and the solution heated for a period of time to allow the bismuth sulfate gluconate complex to form. However, since bismuth sulfate hydrolyzes in water, the bismuth (as bismuth trioxide) is preferably reacted initially with the gluconic acid, with the resulting complex than being reacted with sulfuric acid.

A typical molecular composition in solution of the bismuth sulfate gluconate is illustrated by the formula:

$$3H_2SO_4 \cdot Bi_2(SO_4)_3 \text{ (gluconate)}_9$$

Bismuth sulfate gluconates containing more than nine moles of gluconic acid may also be formed. For example, a bismuth sulfate gluconate may also be prepared which is illustrated by the formula:

$$5H_2SO_4 \cdot Bi_2(SO_4)_3 \text{ (gluconate)}_{12}$$

The process of electroplating the tin-bismuth alloy onto a conductive substrate in accordance with the present invention may be carried out in a conventional manner. For example, the conductive substrate may be a metal such as iron, nickel, stainless steel, zinc, copper, etc., or a combination of two or more of any such metals. Electrodeposition of the tin may be effected using either a soluble or insoluble anode. Insoluble anodes typically are comprised of graphitic carbon or a variety of stainless steel, while soluble anodes may be comprised of tin metal or a tin alloy. Electrodeposition of the tin-containing alloy usually occurs at a temperature within the range of 30° C. to about 60° C. Cathode current densities of about 1 amps/ft$^2$ to about 60 amps/ft$^2$ and preferably from about 15 to 25 amps/ft$^2$ are generally employed.

Electrodeposition of a tin-containing alloy in accordance with this invention is effected by maintaining the conductive substrate as a cathode within the acidic aqueous electroplating baths of the present invention for about 1 to 60 minutes or as long as necessary to provide a tin electroplate of the desired thickness. The electrodeposition of the tin-containing alloy is preferably undertaken for a period of time within this range sufficient to result in an electrotinplate containing from about 0.15 to about 0.80 percent by weight of bismuth to tin, expressed as bismuth metal. It is possible to incorporate as much as 10–14% by weight of bismuth to tin in the plate by adding the required concentration of bismuth in bismuth sulfate gluconate to the bath (e.g. ~21.15 g.p.l. Bi).

Described below in Table I are compositions of electrolyte solutions formulated from a source of tin ions, free sulfuric acid, and a bismuth sulfate gluconate in accordance with this invention which give good performance in electroplating tin-bismuth alloys onto conductive substrates from an acidic electroplating bath. It should be noted that electrolyte solutions prepared in accordance with the present invention are acidic in nature and generally exhibit a pH of 4 or less and preferably less than 1.

TABLE I

| Component | Concentrations (grams/liter) | | |
|---|---|---|---|
| | Broad | Preferred | Typical |
| Stannous tin metal | 10–75 | 15–30 | 19 |
| Free sulfuric acid | 140–215 | 178–214 | 178 |
| Bismuth sulfate gluconate(as Bi metal) | 0.06–21.15 | 0.18–1.02 | 0.375 |

Concentrations of the preferred components of the electroplating baths are as follows:

TABLE II

| Component | Concentrations (grams/liter) | | |
|---|---|---|---|
| | Broad | Preferred | Typical |
| Stannous Sulfate | 18.5–185 | 24–60 | 35 |
| Free sulfuric acid | 140–215 | 178–214 | 178 |
| Bismuth sulfate gluconate(as Bi metal) | 0.06–21.15 | 0.18–1.02 | 0.375 |

The fineness and brightness of the tin plate electroplated from the electrolyte solutions of this invention can be further improved in the usual manner by the addition of various brightening and conditioning agents. It is important, however, not to add such agents in the form of their alkali metal salts. Beta-naphthol at between about 0.5 and 2.0 grams per liter is very effective. Water soluble polyalkylene glycols such as the soluble polyethylene glycols (e.g., "Carbowax 1500," M.W. about 1500) or polypropylene glycols at a concentration of from between 0.5 to 1.0 grams per liter or higher are suitable. These polyglycols typically have a molecular weight of from about 900 to about 6000 but polyglycols of a higher or lower molecular weight may be used. Formamide and dimethyl formamide are useful in concentrations in the range from 0.5 to 20 grams per liter of solution.

Low concentrations of approximately 0.1 to 0.5 grams per liter or more of glue, gelatin, peptones, or inherent components of these substances such as glycine, hydroyproline, lysine, arginine, etc. are effective. Small concentrations of alkyl or aryl amines, e.g. triethylamine, diphenylamine and the like, also can be used to enhance tin plate quality. Conventional additives that tend to coat the cathode, e.g., wood tar extracts, aldehyde amine complexes or any other substance that tends to form tar or a semi-soluble polymeric suspensoid, should be avoided. Such coating of the cathode is undesirable in that it promotes local galvanic action with consequent gas formation, blistering and loss of adhesion of the tin plate.

Exemplary brightening agents are set forth in U.S. Pat. No. 3,616,692, herein fully and completely incorporated by reference. Such brighteners include commercially available brighteners marketed by Vulcan Materials Company under the name "FASAT-TIN" (for satin finish at high speed) and the registered tradename "Bri-Tin" ® (for mirror bright finish).

This invention is additionally illustrated in connection with the following Examples which are to be considered as illustrative of the present invention. It should be understood, however, that the invention is not limited to the specific details of the Examples.

EXAMPLE 1

This example demonstrates a method for producing various bismuth sulfate gluconates and their use in an electrotinplating process.

1A. A Method of Producing $5H_2SO_4 \cdot Bi_2(SO_4)_3$(gluconate)$_{12}$

A weight of 11.2 grams of bismuth trioxide containing 9.08 grams of bismuth is agitated vigorously in a solution of 91.0 milliliters of 50% gluconic acid with the ratio of gluconic acid to bismuth being 6:1. The solution is heated to between 70° and 80° C. and diluted to 200 milliliters. Then 10.5 milliliters of 97% sulfuric acid are added. The resulting clear supernatent yellow-red solution is decanted. The bismuth solution complex formed is $5H_2SO_4 \cdot Bi_2(SO_4)_3(gluconate)_{12}$.

1B. A Method of Producing $3H_2SO_4 \cdot Bi_2(SO_4)_3(gluconate)_9$

A weight of 7.7 grams of ammonium sulfate $(NH_4)_2SO_4$ is dissolved in 272 milliliters of 50% gluconic acid and agitated and heated to about 60° C. A weight of 44.8 grams of bismuth trioxide ($Bi_2O_3$) containing 40 grams of bismuth is slowly added. After 2 hours of admixing at 60° C., 32 milliliters of 97% sulfuric acid is slowly added. The temperature of the solution is raised to about 80° C. The solution is diluted to 70 milliliters two hours later and agitated at 70° C. for 2 more hours. The solution is cooled to room temperature and centrifuged to remove the small amount of residue present. The solution analyzed 48 grams/liter of bismuth having a formula of $3H_2SO_4 \cdot Bi_2(SO_4)_3(gluconate)_9$.

1C. Electroplating With A Plating Bath Containing Bismuth Sulfate Gluconate

A number of liter acid stannous sulfate baths are made up and used for electrotinplating small steel panels. The baths contain brighteners marketed by Vulcan Materials Company under the name "FASAT-TIN" and the tradename "Bri-Tin ®". From 1 to 8 milliliters of an aqueous acidic bismuth sulfate gluconate solution containing not less than 48 grams/liter of bismuth are added to each of the plating baths. The solution also preferably contains free sulfuric acid to aid in the prevention of hydrolysis of the chelate salt. In all instances, the bismuth sulfate gluconate complex dissolves completely without any precipitation and has no appreciable effect on either the bath or the electrotinplate.

A steel panel is then electrotinplated at a moderate cathode current density for a period of time sufficient to accumulate 0.4 to 0.8 grams of tin in each bath. A sample of each plating bath is analyzed for stannous tin and bismuth. The corresponding tin plate electroplated therefrom is analyzed for the presence of tin and bismuth. After a sufficient number of analyses, correlations of the percent bismuth to tin in the tin plate as a function of the percent bismuth to stannous tin in the plating bath are established and are tabulated according to the specific brightener employed in each bath:

| | % BISMUTH TO TIN | |
|---|---|---|
| In Electroplated | In Solution | |
| Tin Plate | Fasat-Tin | Bri-Tin |
| 0.20 | 1.595 | 0.34 |
| 0.25 | 1.913 | 0.432 |
| 0.30 | 2.172 | 0.519 |
| 0.40 | 2.581 | 0.692 |
| 0.50 | 2.898 | 0.865 |
| 0.55 | 3.034 | 0.951 |
| 0.60 | 3.158 | 1.038 |
| 0.70 | 3.377 | 1.210 |

The tin-bismuth electroplated panels are innoculated with alpha tin and exposed to a temperature of −20° C. No tin pest formation is observed.

The acid bismuth sulfate gluconate solutions containing 48 grams/liter of bismuth are thus effective in imparting sufficient bismuth to the tin plate to resist the formation of tin pest.

EXAMPLE 2

A 45 liter acid stannous sulfate bath containing 4 oz./gal. of stannous tin and 10% by volume of concentrated sulfuric acid as well as the Satin brightener was used to barrel plate 0.4 to 0.8 mils of tin on batches of one-half inch size steel cap screws and nuts. The electrotinplate was white satin with excellent covering power and a very fine grain structure.

Then 340 milliliters of an acid bismuth sulfate gluconate solution (48 grams/liter bismuth) are added to the bath to provide 2.22% bismuth to stannous tin. The bismuth solution dissolves completely without any precipitation and imparts a slight tan tint to the bath. The barrel electrotinplating on batches of one-half inch size steel cap screws and nuts is repeated with no diminuation of the quality of the tin plate. Selected tin plated pieces analyzed 0.17 to 0.18% bismuth to tin.

Groups of the cap screws and nuts with and without bismuth were selected and two pieces in each of the four groups of six pieces were pressure innoculated with alpha tin previously demonstrated to be very effective in promoting tin pest. The groups were placed in polyethylene bags and stored in a deep freezer at −20° C. After being stored in the freezer for a month, the electrotinplates containing bismuth showed no signs of growth or propogation of tin pest (i.e., alpha tin or "tin disease") while the electrotinplates which did not contain bismuth were almost completely transformed to tin pest and had spalled off the steel substrate. The acid bismuth sulfate gluconate solutions added to acid stannous sulfate electrotinplating baths also suppressed outgrowths from the electrotinplate (i.e., "tin whiskers").

The principles, preferred embodiments, and modes of operation of the present invention have been described in the foregoing specification. The invention which is intended to be protected herein, however, is not to be construed or limited to the particular forms disclosed, since these are to be regarded as illustrative rather than restrictive. Variations and changes may be made by those skilled in the art without departing from the spirit of the invention.

I claim:

1. A method of electroplating a tin and bismuth-containing alloy onto a conductive substrate comprising immersing a conductive substrate to be plated into an aqueous acidic plating bath containing tin ions, free sulfuric acid and a chelate salt comprising bismuth sulfate gluconate, and electroplating a tin and bismuth-containing alloy onto said conductive substrate as a cathode in the bath.

2. The method of claim 1 wherein said tin ions are provided by stannous sulfate.

3. The method of claim 1 wherein the aqueous acidic plating bath contains between about 0.06 to about 21.15 grams per liter of bismuth metal as bismuth sulfate gluconate.

4. The method of claim 1 wherein said bismuth sulfate gluconate is represented by the formula $3H_2SO_4 \cdot Bi_2(SO_4)_3(gluconate)_9$.

5. The method of claim 1 wherein said bismuth sulfate gluconate is represented by the formula $5H_2SO_4 \cdot Bi_2(SO_4)_3(gluconate)_{12}$.

6. The method of claim 1 wherein said conductive substrate is immersed in said bath and said tin and bismuth-containing alloy is electroplated thereon for a period of time sufficient to provide an electroplated alloy containing from about 0.15 to about 0.80 percent by weight of bismuth as bismuth metal.

7. The method of claim 1 wherein the pH of said acidic bath is less than 4.

8. The method of claim 1 wherein said acidic bath contains a brightening agent.

9. A method of electroplating a tin and bismuth-containing alloy onto a conductive substrate comprising immersing a conductive substrate to be plated into an acidic aqueous plating bath containing tin ions in an amount ranging between about 10 to about 75 grams per liter, free sulfuric acid in an amount ranging between about 140 to about 215 grams per liter, and a chelate salt comprising bismuth sulfate gluconate in an amount ranging between about 0.06 to about 21.15 grams per liter expressed as bismuth metal, and electroplating a tin and bismuth-containing alloy onto said conductive substrate as a cathode in said bath.

10. The method of claim 9 wherein said conductive substrate is immersed in said bath and said tin and bismuth-containing alloy is electroplated thereon for a period of time sufficient to provide an electroplated alloy containing from about 0.15 to about 0.80 percent by weight of bismuth as bismuth metal.

11. The method of claim 9 wherein said tin ions are provided by stannous sulfate.

12. An aqueous acidic solution for plating a tin and bismuth-containing alloy onto a conductive substrate which solution comprises tin ions, free sulfuric acid and an acid chelate comprising bismuth sulfate gluconate.

13. The aqueous solution of claim 12 wherein said tin ions are provided by stannous sulfate.

14. The aqueous solution of claim 12 which comprises from about 0.06 to about 21.15 grams per liter of bismuth metal as bismuth sulfate gluconate.

15. The solution of claim 12 wherein said bismuth sulfate gluconate is represented by the formula $3H_2SO_4 \cdot Bi_2(SO_4)_3(gluconate)_9$.

16. The solution of claim 12 wherein said bismuth sulfate gluconate is represented by the formula $5H_2SO_4 \cdot Bi_2(SO_4)_3(gluconate)_{12}$.

17. The solution of claim 12 wherein the pH of said solution is less than 4.

18. The solution of claim 12 wherein said tin ions are present in an amount ranging from about 10 to about 75 grams per liter.

19. A composition for use in the plating of a bismuth-containing alloy comprising an aqueous solution of a chelate salt comprising bismuth sulfate gluconate.

20. The composition of claim 19 wherein said aqueous solution is acidic.

21. The composition of claim 19 wherein said aqueous solution further comprises sulfuric acid.

22. The composition of claim 19 wherein said bismuth sulfate gluconate is represented by the formula $3H_2SO_4 \cdot Bi_2(SO_4)_3(gluconate)_9$.

23. The composition of claim 19 wherein said bismuth sulfate gluconate is represented by the formula $5H_2SO_4 \cdot Bi_2(SO_4)_3(gluconate)_{12}$.

* * * * *